United States Patent
Mihara

(10) Patent No.: US 7,248,792 B2
(45) Date of Patent: Jul. 24, 2007

(54) DENTAL WATER HEATER

(75) Inventor: Fukuhisa Mihara, Kanuma (JP)

(73) Assignee: Nakanishi Inc., Kanuma-shi (JP)

( * ) Notice: Subject to any disclaimer, the term of this patent is extended or adjusted under 35 U.S.C. 154(b) by 143 days.

(21) Appl. No.: 11/224,228

(22) Filed: Sep. 13, 2005

(65) Prior Publication Data

US 2006/0056571 A1   Mar. 16, 2006

(30) Foreign Application Priority Data

Sep. 14, 2004   (JP) .............................. 2004-267060

(51) Int. Cl.
    *F24H 1/10*   (2006.01)
(52) U.S. Cl. ...................... 392/492; 392/465; 392/481
(58) Field of Classification Search ................. 392/492
    See application file for complete search history.

(56) References Cited

U.S. PATENT DOCUMENTS

| 1,356,818 | A | * | 10/1920 | Hadaway, Jr. .............. 392/396 |
| 1,519,395 | A | * | 12/1924 | Clench ...................... 392/493 |
| 1,671,677 | A |   | 5/1928  | Keeton |
| 1,716,996 | A | * | 6/1929  | Adam ....................... 392/481 |
| 1,724,767 | A | * | 8/1929  | Mercer ...................... 392/481 |
| 1,985,830 | A | * | 12/1934 | Powers ...................... 392/492 |
| 2,576,558 | A | * | 11/1951 | Bede ......................... 392/495 |
| 3,584,194 | A | * | 6/1971  | Kautz et al. ................. 392/484 |
| 3,835,294 | A | * | 9/1974  | Krohn et al. ................ 392/484 |
| 4,286,140 | A |   | 8/1981  | Dewulf et al. |
| 4,465,922 | A | * | 8/1984  | Kolibas ...................... 392/484 |
| 4,604,515 | A | * | 8/1986  | Davidson .................... 392/492 |
| 5,257,341 | A |   | 10/1993 | Austin, Jr. et al. |
| 5,265,318 | A | * | 11/1993 | Shero ......................... 29/447 |

FOREIGN PATENT DOCUMENTS

NL   44509   6/1938

* cited by examiner

*Primary Examiner*—Thor S. Campbell
(74) *Attorney, Agent, or Firm*—Hahn & Voight PLLC

(57) ABSTRACT

The present invention relates to a dental water heater. The water heater has a columnar body, and the body includes heating means extending in the axial direction of the body, and a plurality of layers of water channel sections arranged around the heating means. Each of the water channel sections spirally extends in the axial direction of the body. The adjacent pairs of the water channel sections are communicated either at upper or lower end portions thereof so as to together form a whole water channel. The whole water channel has an inlet and an outlet for water to be heated, so that water is supplied through the inlet, passed through the entire length of the whole water channel, and taken out as warmed water through the outlet.

5 Claims, 2 Drawing Sheets

(a)

(b)

DENTAL WATER HEATER

FIELD OF ART

The present invention relates to a dental water heater, in particular to a water heater for warming water to be supplied to a dental treatment apparatus that is capable of injecting water in the oral cavity of a patient.

BACKGROUND ART

In cutting teeth during dental treatment, water is sprayed onto the cutting site for reducing friction resistance between the cutting tip and teeth or removing debris. Water is also used for rinsing oral cavity during dental treatment, or washing treatment site with water spray. Water used for such purposes is usually tap water, which is relatively cold. Thus when the water gets into the treatment site or decayed teeth, the patient may feel pain.

In order to solve this problem, water heaters are used for warming water before use. However, conventional water heaters are relatively large or require a large space for installment. Some heaters are even insufficient in heat efficiency in warming water.

SUMMARY OF THE INVENTION

The present invention aims to solve these problems of conventional water heaters. It is therefore an object of the present invention to provide a dental water heater that is relatively restricted in volume and thus installable in a relatively small space, and dissipates only a little heat to outside, resulting in excellent heat efficiency.

According to the present invention, there is provided a dental water heater having a columnar body, said body comprising heating means extending in the axial direction of said body, and a plurality of layers of water channel sections arranged around said heating means, each of said water channel sections spirally extending in the axial direction of said body, wherein adjacent pairs of said water channel sections are communicated either at upper or lower end portions thereof so as to together form a whole water channel, and wherein said whole water channel has an inlet and an outlet for water to be heated, so that water is supplied through said inlet, passed through the entire length of said whole water channel, and taken out as warmed water through said outlet.

In the dental water heater of the present invention, while the water supplied through the inlet is passed through the entire length of the whole water channel, the water is warmed with the heat from the heating means, and taken out through the outlet. Since the whole water channel is formed of a plurality of water channel sections each extending spirally and arranged in layers, a relatively long water channel may be formed in the body of a relatively small volume. This secures sufficient length of way (duration) for the water to receive heat from the heating means, and remarkably improves heat efficiency of a dental water heater.

In a preferred embodiment of the present invention, the plurality of layers of water channel sections may be communicated such that water supplied to the outermost layer of the water channel section flows serially in each layer inwardly to the innermost layer of the water channel section.

In this embodiment, the water to be heated flows from the water channel section of the outermost layer, which is located farthest from the heating means, gradually inwardly layer by layer toward the heating means, to the water channel section of the innermost layer, which is located closest to the heating means. Thus the amount of heat given from the heating means to the water of relatively low temperature gradually increases as the water flows inwardly through the whole water channel, and the heat is efficiently transmitted to the water. Thus warmed water is produced with excellent heat efficiency.

In a preferred embodiment of the present invention, the inlet for water may be provided in the water channel section of the outermost layer, and the outlet for water maybe provided in the water channel section of the innermost layer.

In this embodiment, the water to be heated flows from the water channel section of the outermost layer toward the water channel section of the innermost layer, so that the amount of heat given from the heating means to the water gradually increases. Thus heat from the heating means is transferred to the water with excellent heat efficiency.

According to the present invention, the plurality of layers of water channel sections may be arranged coaxially with the heating means and with each other, and/or the adjacent pairs of the water channel sections may be communicated through at least one communication port.

PREFERRED EMBODIMENTS OF THE INVENTION

The present invention will now be explained with reference to a preferred embodiment of the present invention taken in conjunction with the attached drawings, which is illustrative only and does not intend to limit the present invention.

Figure 1:
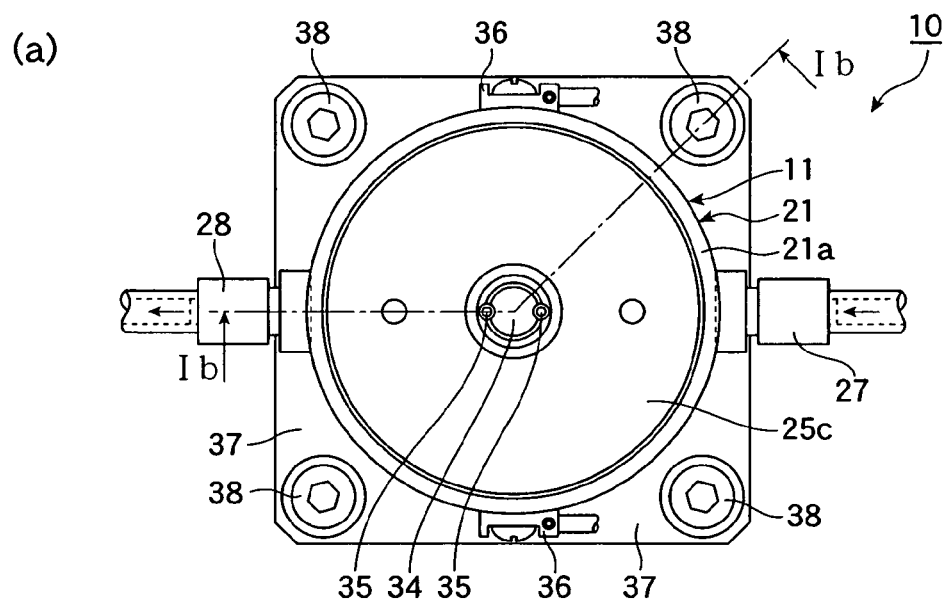
FIG. 1(a) is a plan view of an embodiment of the dental water heater according to the present invention.
FIG. 1(b) is a longitudinal sectional view taken along lines Ib-Ib in FIG. 1(a).
Figure 1:
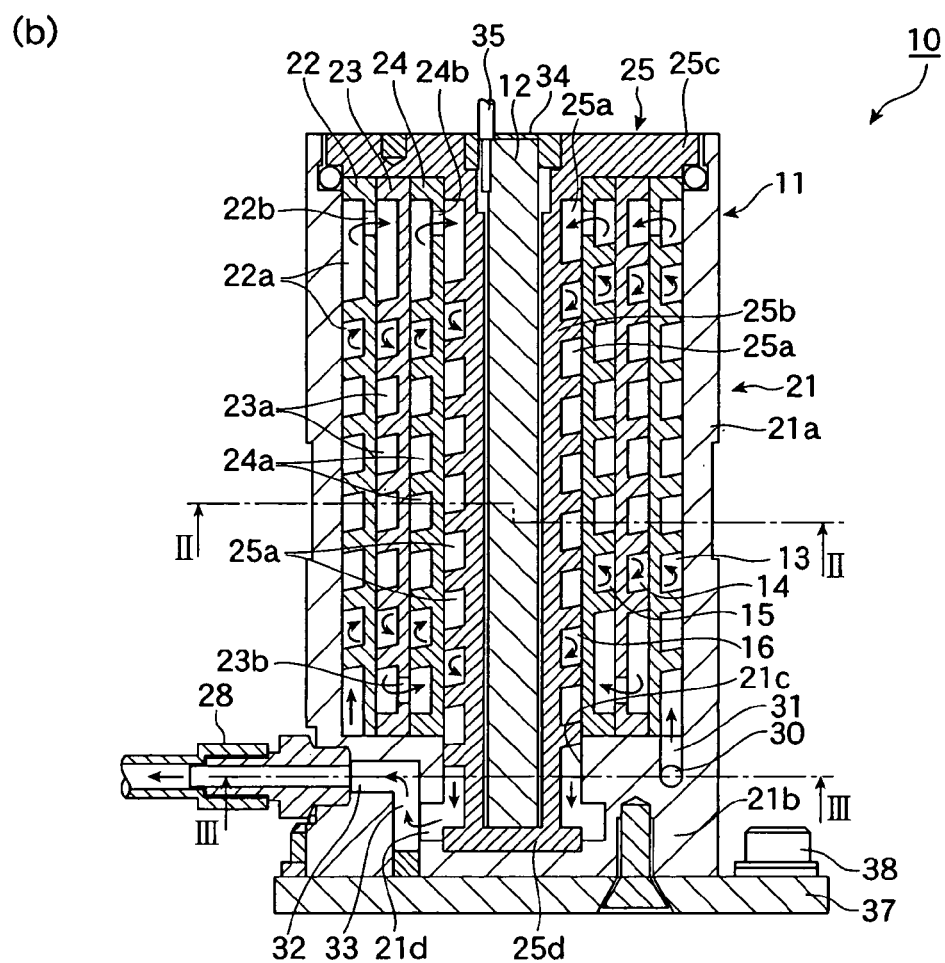

Referring to FIG. 1, dental water heater 10 of the present invention has body 11 formed in a generally columnar shape. Heater 12 is provided in the body 11 and extends in the axial direction of the body 11. Around the heater 12 in the body 11, first to fourth water channel sections 13 to 16 are arranged in a plurality of layers coaxially with the heater 12 and with each other, and each of the water channel sections 13 to 16 extends spirally in the axial direction of the body 11. The adjacent pairs of these water channel sections 13 to 16 are communicated with each other either at the upper or lower end portions thereof, to thereby form a whole water channel together. The whole water channel formed of the water channel sections 13 to 16 is provided with at least one inlet and at least one outlet for the water to be heated, so that the water is supplied through the inlet, flows through the entire length of the whole water channel, and taken out through the outlet as warmed water.

More specifically, referring to FIG. 1(b), the body 11 of the present dental water heater includes generally cylindrical casing 21, inside of which first water channel defining member 22 is inserted and snugly fitted. Inside the first water channel defining member 22, in turn, second water channel defining member 23 is inserted and snugly fitted. Inside the second water channel defining member 23, in turn, third water channel defining member 24 is inserted and snugly fitted. Inside the third water channel defining member 24, in turn, fourth water channel defining member 25 is inserted and snugly fitted.

The first to third water channel defining members 22 to 24 are generally cylindrical members having spiral channels 22a to 24a, respectively, formed in the outer surface thereof. The fourth water channel defining member 25 includes generally cylindrical portion 25b having spiral channel 25a formed in the outer surface thereof, and lid 25c formed integrally with the cylindrical portion 25b for closing the upper end of the cylindrical casing 21. The cylindrical portion 25b of the fourth water channel defining member 25 is formed slightly longer than the first to third water channel defining members 22 to 24. The lower end of the cylindrical portion 25b is closed with bottom portion 25d, and the heater 12 is placed inside the cylindrical portion 25b.

Figure 2:
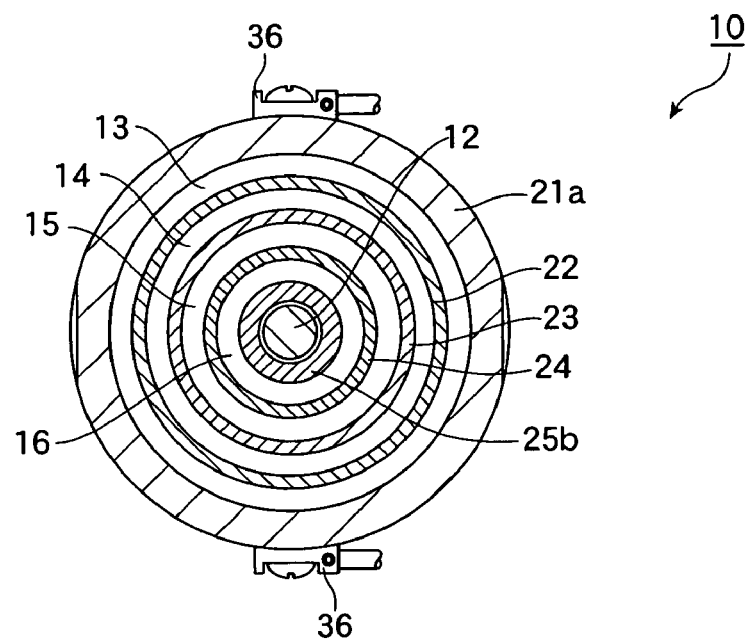
FIG. 2 is a cross-sectional view taken along lines II-II in FIG. 1(b).

As shown in FIGS. 1(b) and 2, the first water channel section 13 is defined by the spiral channel 22a in the fist water channel defining member 22 and the inner surface of the cylindrical casing 21 that closes the channel 22a. The second water channel section 14 is defined by the spiral channel 23a in the second water channel defining member 23 and the inner surface of the first water channel defining member 22 that closes the channel 23a. The third water channel section 15 is defined by the spiral channel 24a in the third water channel defining member 24 and the inner surface of the second water channel defining member 23 that closes the channel 24a. The fourth water channel section 16 is defined by the spiral channel 25a in the fourth water channel defining member 25 and the inner surface of the third water channel defining member 24 that closes the channel 25a.

The first water channel defining member 22 has at least one communication port 22b penetrating the member 22 in the upper end portion of the spiral channel 22a, and similarly, the third water channel defining member 24 has at least one communication port 24b penetrating the member 24 in the upper end portion of the spiral channel 24a. The second water channel defining member 23 has at least one communication port 23b penetrating the member 23 in the lower end portion of the spiral channel 23a.

The first water channel section 13 communicates with the second water channel section 14 via the first communication ports 22b in the upper end portion thereof, the second water channel section 14 communicates with the third water channel section 15 via the second communication ports 23b in the lower end portion thereof, and the third water channel section 15 communicates with the fourth water channel section 16 via the third communication ports 24b in the upper end portion thereof. The first to fourth water channel sections 13 to 16 thus communicated together form a whole water channel.

Figure 3:
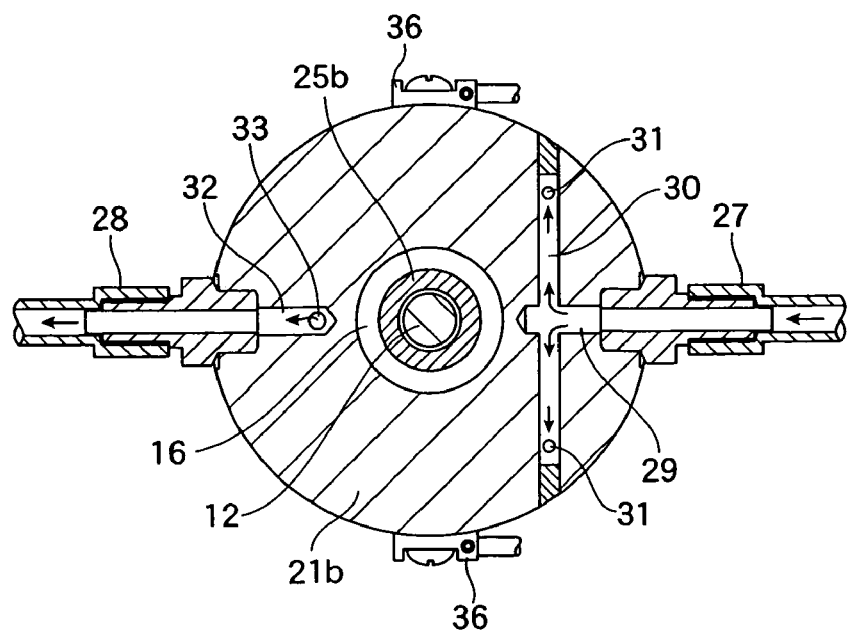
FIG. 3 is a cross-sectional view taken along lines III-III in FIG. 1(b).

As shown in FIG. 1(b), the cylindrical casing 21 has cylindrical portion 21a and bottom portion 21b that closes the lower end of the cylindrical portion 21a. The bottom portion 21b has dent 21c formed generally in the center thereof for receiving the lower end portion of the cylindrical portion 25b of the fourth water channel defining member 25, and fourth communication port 21d formed through the bottom portion 21b and communicating with the dent 21c. The bottom portion 21b of the casing 21 is also provided with two hose connecting members 27 and 28 in its outer periphery, and one of the hose connecting members 27 is used as an inlet member for supplying water to be heated into the body 11, while the other 28 as an outlet member for discharging the warmed water from the body 11. As shown in FIG. 3, the hose connecting member 27 as an inlet member is communicated with the lower end portion of the first water channel section 13 via attachment hole 29 for the member 27, transverse channels 30, and vertical channels 31. The hose connecting member 28 as an outlet member is communicated with the lower end portion of the fourth water channel 16 via attachment hole 32 for the member 28, vertical channel 33, and the fourth communication port 21d.

The cylindrical portion 25b of the fourth water channel defining member 25 receives the heater 12 inserted therein, which is fixed therein with an adhesive, and the top of the portion 25b is closed with lid 34. Electric cables 35 connected to the heater 12 extend through the lid 34 to outside.

Temperature sensors 36 are attached to the outer surface of the cylindrical casing 21 of the body 11 for detecting the temperature of the cylindrical portion 21a of the casing 21 to control the temperature of the heater 12. The body 11 is fixed to heat insulating base 37 with screws or the like means, and the base 37 is fixed, in turn, on an installation surface of a dental apparatus or the like with screws 38 or the like means.

The flow pathway of water to be heated in the dental water heater 10 is explained below.

Water to be heated is supplied from an external source, such as a tap, and introduced into the dental water heater 10 through the hose connecting member 27. The water taken in through the hose connecting member 27 is then passed through the attachment hole 29, branched into the transverse channels 30, passed up through the respective vertical channels 31 as shown in FIG. 3, and led to the lower end portion of the first water channel section 13 as shown in FIG. 1(b). From here, the water spirally rises through the first water channel section 13 up to the first communication ports 22b in the upper end portion thereof, through which it flows into the upper end portion of the second water channel section 14. The water then spirally descends through the second water channel section 14 down to the second communication ports 23b in the lower end portion thereof, through which it flows into the lower end portion of the third water channel section 15. Again, the water spirally rises through the third water channel section 15 up to the third communication ports 24b in the upper end portion thereof, through which it flows into the upper end portion of the fourth water channel section 16. Then the water spirally descends through the fourth water channel section 16 down to its lower end, passes through the fourth communication port 21d formed through the bottom portion 21b of the casing 21, up through the vertical channel 33, and through the attachment hole 32, and taken out through the hose connecting member 28 as warmed water. The warmed water thus discharged from the dental water heater 10 is then supplied to a dental treatment apparatus for spraying into the oral cavity of a patient.

Although the present invention has been described with reference to the preferred embodiment, it should be understood that various modifications and variations can be easily made by those skilled in the art without departing from the spirit of the invention.

For example, in the embodiment described above, the first to third water channel defining members 22 to 24 are shown to have two communication ports 22b to 24b, respectively, and the fourth water channel defining member 25 is shown to have one communication port 21d, in the sectional view of FIG. 1(b). Further, the first and third communication ports 22b and 24b are provided in the upper end portion of the first and third water channel defining members 22 and 24, respectively, and the second and fourth communication ports 23b and 21d are provided in the lower end portion of the second and fourth water channel defining members 23 and 25, respectively. However, the number and location of the first to fourth communication ports 22*b* to 24*b* and 21*d* may be selected as desired without departing from the spirit of the present invention. The whole water channel is shown to have two inlets for water communicating with two vertical channels 31 and one outlet for water communicating with the vertical channel 33 in the drawings, and both the inlets and the outlet are provided in the lower end portions of the water channel sections 13 and 16, respectively. However, the number and location of the inlet and outlet may be selected as desired without departing from the spirit of the present invention, and either of the inlet or outlet or both of them may be provided in the upper end portions of the water channel sections 13 and 16, respectively.

Accordingly, the foregoing disclosure should be interpreted as illustrative only and is not to be interpreted in a limiting sense. The present invention is limited only by the scope of the following claims.

What is claimed is:

1. A dental water heater having a columnar body, said body comprising:

heating means extending in the axial direction of said body, and a plurality of layers of water channel sections arranged around said heating means, each of said water channel sections spirally extending in the axial direction of said body, wherein adjacent pairs of said water channel sections are communicated either at upper or lower end portions thereof so as to together form a whole water channel, and wherein said whole water channel has an inlet and an outlet for water to be heated, so that water is supplied through said inlet, passed through the entire length of said whole water channel, and taken out as warmed water through said outlet.

2. The dental water heater of claim 1, wherein said plurality of layers of water channel sections are communicated such that water supplied to the outermost layer of the water channel section flows serially in each layer inwardly to the innermost layer of the water channel section.

3. The dental water heater of claim 1, wherein said inlet for water is provided in the water channel section of the outermost layer, and said outlet for water is provided in the water channel section of the innermost layer.

4. The dental water heater of claim 1, wherein said plurality of layers of water channel sections are arranged coaxially with said heater means and with each other.

5. The dental water heater of claim 1, wherein said adjacent pairs of water channel sections are communicated through at least one communication port.

* * * * *